United States Patent
Auriel et al.

(10) Patent No.: US 12,043,423 B2
(45) Date of Patent: Jul. 23, 2024

(54) OPTIMISED METHOD FOR FILLING A PYROTECHNIC CHARGE AND SYSTEM IMPLEMENTING SUCH A METHOD

(71) Applicant: CROSSJECT, Dijon (FR)

(72) Inventors: Christophe Auriel, Binges (FR); Stéphane Monnier, Dijon (FR); Michel Cavillon, Dijon (FR); Maxime Ressouche, Dijon (FR)

(73) Assignee: CROSSJECT, Dijon (FR)

( * ) Notice: Subject to any disclaimer, the term of this patent is extended or adjusted under 35 U.S.C. 154(b) by 357 days.

(21) Appl. No.: 17/603,788

(22) PCT Filed: Apr. 15, 2020

(86) PCT No.: PCT/EP2020/060591
§ 371 (c)(1),
(2) Date: Oct. 14, 2021

(87) PCT Pub. No.: WO2020/212422
PCT Pub. Date: Oct. 22, 2020

(65) Prior Publication Data
US 2022/0196373 A1    Jun. 23, 2022

(30) Foreign Application Priority Data
Apr. 15, 2019   (FR) ..................... 19/04010

(51) Int. Cl.
*F42B 33/02*    (2006.01)
*B65B 1/08*    (2006.01)
(Continued)

(52) U.S. Cl.
CPC .................. *B65B 1/34* (2013.01); *B65B 1/08* (2013.01); *G01G 13/026* (2013.01);
(Continued)

(58) Field of Classification Search
CPC .......... B65B 1/24; B65B 1/08; G01G 13/026; A61M 5/2046; A61M 2005/208; F42B 33/0207; F42B 33/0285
(Continued)

(56) References Cited

U.S. PATENT DOCUMENTS

| | | | | |
|---|---|---|---|---|
| 4,111,272 A | * | 9/1978 | Ricciardi | G05D 7/0605 177/121 |
| 5,092,413 A | * | 3/1992 | Andrews | G01G 13/026 177/56 |

(Continued)

FOREIGN PATENT DOCUMENTS

| | | | |
|---|---|---|---|
| CA | 2749632 A1 | * | 8/2011 |
| CN | 105565007 A | | 5/2016 |

(Continued)

OTHER PUBLICATIONS

Jul. 10, 2020 International Search Report issued in International Patent Application No. PCT/EP2020/060591.
(Continued)

*Primary Examiner* — Bob Zadeh
(74) *Attorney, Agent, or Firm* — Oliff PLC

(57) ABSTRACT

A method for filling a container with a pyrotechnic charge using a filling system, said method including, when the powder is conveyed, a step of regulating the powder flow rate in which at least one powder conveyor device is brought to vibrate according to a vibration frequency control sequence, the vibration frequency being inversely proportional to the filling ratio of the container of the pyrotechnic charge.

14 Claims, 3 Drawing Sheets

Figure 1:
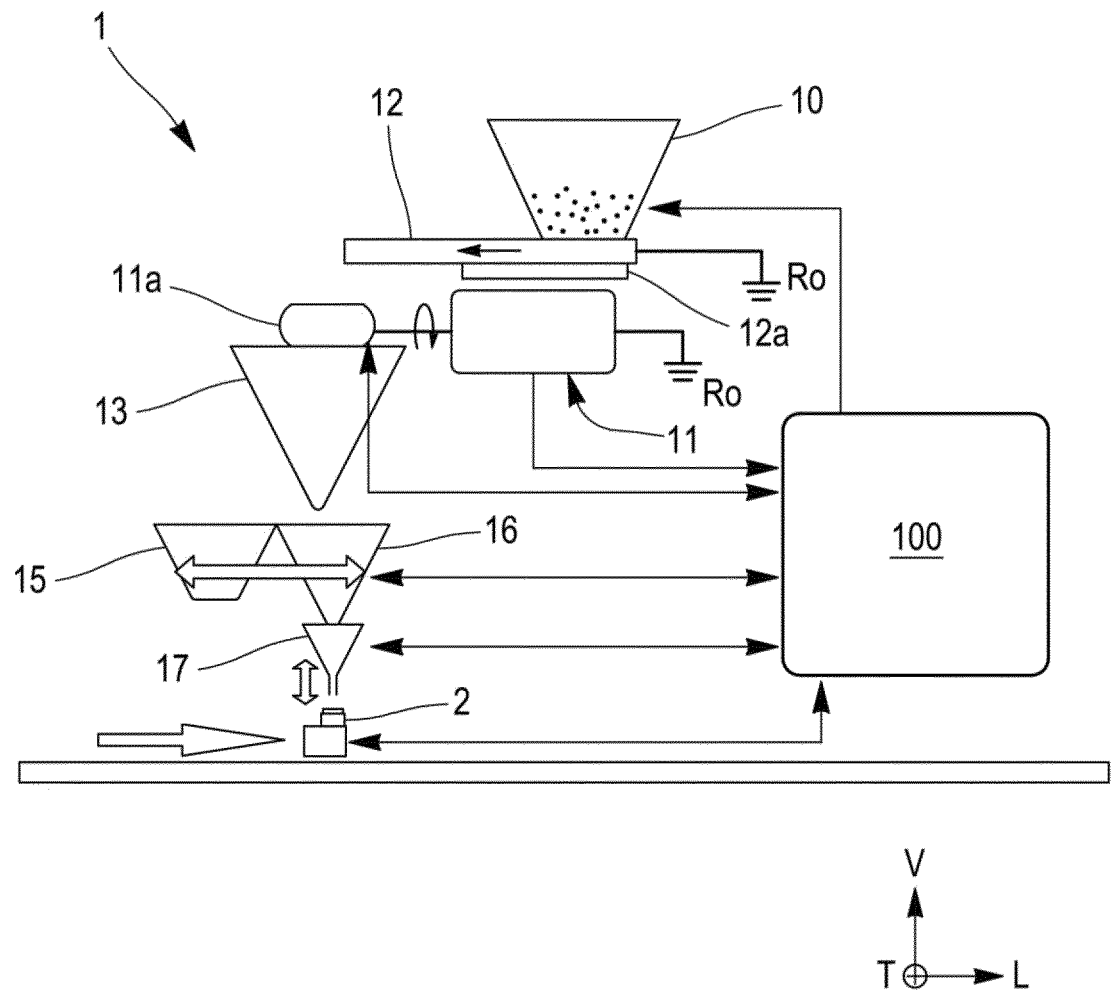

(51) Int. Cl.
  *B65B 1/34* (2006.01)
  *G01G 13/02* (2006.01)
  *A61M 5/20* (2006.01)
(52) U.S. Cl.
  CPC ..... *A61M 5/2046* (2013.01); *A61M 2005/208* (2013.01); *F42B 33/0207* (2013.01); *F42B 33/0285* (2013.01)
(58) Field of Classification Search
  USPC .................................... 222/57–59, 50, 55
  See application file for complete search history.

(56) References Cited

U.S. PATENT DOCUMENTS

| | | | |
|---|---|---|---|
| 6,121,556 | A | 9/2000 | Cole |
| 6,474,372 | B2 * | 11/2002 | Sanderson .............. B29B 7/244 |
| | | | 177/105 |
| 6,964,650 | B2 | 11/2005 | Alexandre et al. |
| 7,259,338 | B2 | 8/2007 | Sugioka et al. |
| 2011/0198197 | A1 * | 8/2011 | Blickley .................. B29B 7/60 |
| | | | 73/861.351 |
| 2013/0054017 | A1 * | 2/2013 | Horev .................... G06M 7/00 |
| | | | 700/240 |
| 2022/0196373 | A1 * | 6/2022 | Auriel ..................... B65B 1/34 |

FOREIGN PATENT DOCUMENTS

| | | |
|---|---|---|
| DE | 4405253 A1 | 10/1994 |
| FR | 2815544 A1 | 4/2002 |
| JP | S59-91318 A | 5/1984 |
| JP | H11-130001 A | 5/1999 |
| JP | 2004-284634 A | 10/2004 |
| JP | 2004-532049 A | 10/2004 |
| JP | 2005-089088 A | 4/2005 |
| JP | 2005-156354 A | 6/2005 |
| JP | 2014-214962 A | 11/2014 |
| JP | 2017-100792 A | 6/2017 |
| SE | 420949 B | 11/1981 |

OTHER PUBLICATIONS

Jul. 10, 2020 Written Opinion issued in International Patent Application No. PCT/EP2020/060591.

* cited by examiner

OPTIMISED METHOD FOR FILLING A PYROTECHNIC CHARGE AND SYSTEM IMPLEMENTING SUCH A METHOD

The invention relates to a method for filling a pyrotechnic charge. The invention also relates to a filling system that could implement said method.

The filling method and system according to the invention find application in the general field of filling a pyrotechnic charge.

The filling method and system according to the invention finds particular application when they are applied to a needleless injection device comprising such a pyrotechnic charge.

There are known pre-filled and disposable needleless injection devices operating with an energy source such as for example a gas generator, and used for intradermal, subcutaneous and intramuscular injections of an active substance intended for a therapeutic use in human or veterinary medicine.

The active substance is constituted by a liquid which could be viscous, a mixture of liquids, or a gel. The active substance may also consist of a solid dissolved in a suitable solvent for injection or be constituted by a pulverulent solid in suspension at a determined concentration in a suitable liquid.

Such an injection device includes, in a known manner, for example in the patent application FR 2 815 544 A, a body comprising successively a gas generator, an expansion chamber, a reservoir containing the active substance and an injection system.

Such a gas generator includes a container receiving a bi-composition mixture of powders formed by a live powder and by a slow powder.

The reservoir is inserted into a tubular housing of the body of the injection device, while being sealed by an upper, or upstream, plunger and a lower, or downstream, plunger. The lower free end of the reservoir cooperates with the injection system comprising an injection nozzle including several injection channels extending axially along an injection axis. The diameter of the injection channels is compliant with the grain-size distribution of the active substance to avoid the latter being sealed.

To enable the injection of the active substance, the body is slidably mounted in a hollow cowl wrapping the body, from the bottom to the top along a slide axis, between a rest position and an injection position, driving of the body being performed when the user presses the injection nozzle on his skin. The displacement of the body in the cowl enables triggering of the gas generator, generating a pressurised gas which causes a displacement of the plungers to inject the active substance through the skin of the patient, throughout the injection nozzle.

In this injection position, the active substance is ejected from the channels of the injection nozzle, in an injection direction, according to jets having a predetermined injection pressure enabling the active substance to cross the skin of the patient to the desired depth to ensure an optimum injection of the latter. Hence, the injection pressure of these jets determines the injection depth of the injected active substance in the skin.

To allow for a successful injection, the jets at the outlet of the injection nozzle should be delivered according to this injection pressure over a predetermined injection time guaranteeing the injection of the desired amount of active substance.

Of course, these pressure amplitude, or alternatively the injection pressure and injection time amplitudes, depend on the active substance to be injected.

Thus, each of the powders of the pyrotechnic charge should be accurately dosed in each container. For example, the accuracy of dosage of the live powder may be substantially equal to 1 mg, while the accuracy of the slow powder may be substantially equal to 2 mg.

When it is desired to maintain an optimum production rate for the mass production of pyrotechnic charges, it has been noticed that the powder of some pyrotechnic charges is wrongly dosed, leading to a non-compliance of the injection devices on which these pyrotechnic charges are mounted.

Consequently, it is common to reduce the production rate to accurately dose the pyrotechnic charges, thereby limiting the production of pyrotechnic charge batches while still accepting a reduced number of non-compliant pyrotechnic charges.

Hence, there is a need for an optimised method for filling a pyrotechnic charge allowing dosing such a pyrotechnic charge accurately while ensuring an optimum production rate.

To this end, an object of the invention is a method for filling a container with a pyrotechnic charge using a filling system, the filling system comprising at least:
- a reservoir for dispensing a pyrotechnic powder,
- a device for measuring this powder, and
- a device for conveying this powder from the reservoir up to a basin of the measuring device, said method comprising:
- when the powder is conveyed, a step of regulating the powder flow rate in which the at least one powder conveyor device is brought to vibrate according to a vibration frequency control sequence, the vibration frequency being inversely proportional to the filling ratio of the container of the pyrotechnic charge.

Thanks to such a filling method, it is possible to ensure a constant and accurate distribution of the powder into the basin of the measuring device.

By filling ratio of the container of the pyrotechnic charge, it should be understood the ratio between the measured amount of powder in the basin and the desired amount of powder in the container of the pyrotechnic charge.

The desired amount of powder corresponds to a predetermined weight setpoint value, more or less a predetermined tolerance.

For example, the desired amount of powder in the container of the pyrotechnic charge may vary from 8 mg to 60 mg.

For example, the predetermined tolerance is comprised between 0.25 mg and 2 mg. For example, the predetermined tolerance is 0.5 mg. In another example, the predetermined tolerance is 1 mg.

Advantageously, the basin may then allow preparing the desired amount of powder in the pyrotechnic charge while the container is conveyed on the production line.

In other words, such a method allows preparing the desired amount of powder that has to be poured into the container independently of the latter. Thus, when the measured amount of powder is larger than a predetermined threshold value, the wrongly dosed powder may be collected without having to identify the container as non-compliant. Indeed, the wrongly dosed powder could thus be recovered and could be introduced again into the dispenser reservoir.

According to one aspect, the maximum size of the grains of the powder is calibrated by a sieve placed upstream of the conveyor device.

Indeed, when a command for stopping the transfer of powder into the basin of the measuring device is given, a determined lag time elapses before a last grain falls into the basin. This due to both the response time of an acquisition chain of a piece of information received by a controller of the filling system and to the inertia of the grains. This lag time generates an uncertainty on the amount of powder conveyed into the basin. The sieve disposed upstream of the conveyor device allows limiting this uncertainty.

According to a variant of the method of the invention, the vibration frequency control sequence may comprise a first phase in which the powder conveyor device is brought to vibrate according to a first frequency until reaching a first filling ratio of the container.

For example, the first filling ratio of the container is comprised between 50% and 80%, preferably at least equal to 70%.

According to one aspect, the vibration frequency control sequence may comprise a second phase, subsequent to the first phase, in which the powder conveyor device is brought to vibrate according to a second frequency until reaching a second filling ratio of the container.

For example, the second filling ratio of the container is higher than 80%. For example, the second filling ratio of the container is higher than 90%.

According to one aspect, the first frequency is higher than the second frequency.

For example, the first frequency is comprised between 16 Hz and 18 Hz. For example, the first frequency is substantially equal to 17 Hz.

For example, the second frequency is comprised between 13 Hz and 16 Hz. For example, the second frequency is substantially equal to 15 Hz.

According to one aspect, the vibration frequency control sequence may comprise a third phase, called «stabilisation phase», in which setting of the conveyor device in vibration is stopped until stabilisation of the measured amount of powder. For example, the third stabilisation phase has a duration comprised between 1000 ms and 3000 ms. For example, the third stabilisation phase has a duration substantially equal to 2000 ms.

If, once stabilised, the measured amount of powder corresponds to the desired amount of powder or is larger than the desired amount of powder, the vibration frequency control sequence of the conveyor device is terminated.

If, once stabilised, the measured amount of powder is smaller than the desired amount of powder following the third phase, it may be provided for a fourth phase comprising setting the powder conveyor device in vibration according to a third frequency over a predetermined time period.

For example, the fourth phase is implemented when the filling ratio is comprised between 95 and 98%.

It should be noted that the fourth phase is implemented when, after the third phase, the measured amount of powder is smaller than the predetermined setpoint value less the predetermined tolerance.

For example, the predetermined duration of the fourth phase is comprised between 500 ms and 1500 ms. For example, the predetermined duration of the fourth phase is substantially equal to 1000 ms.

For example, the third frequency is comprised between 10 Hz and 20 Hz. For example, the third frequency is substantially equal to 14 Hz.

According to one aspect, between the second phase and the third phase, the vibration frequency control sequence may comprise a second similar phase in which the powder conveyor device is brought to vibrate according to a second similar frequency until reaching a second similar filling ratio of the container.

For example, the second similar filling ratio is higher than 95%.

For example, the second similar frequency is lower than the second frequency. For example, the second similar frequency is comprised between 8 Hz and 13 Hz. For example, the second similar frequency is substantially equal to 10 Hz.

According to one aspect, subsequently to the fourth phase, the vibration frequency control sequence may comprise a fifth stabilisation phase, in which setting the powder conveyor device in vibration is stopped until stabilisation of the measured amount of powder.

For example, the fifth stabilisation phase has a duration comprised between 1000 ms and 3000 ms. For example, the third stabilisation phase has a duration of about 2000 ms.

If, once stabilised, the measured amount of powder corresponds to the desired amount of powder or is larger than the desired amount of powder, the vibration frequency control sequence of the conveyor device is terminated.

If, once stabilised, the measured amount of powder is smaller than the desired amount of powder, the fourth phase and the fifth phase are repeated until the measured amount of powder corresponds, once stabilised, to the desired amount of powder.

According to one aspect, prior to the first phase, the vibration frequency control sequence may comprise a start-up phase, in which the powder conveyor device is brought to vibrate according to a start-up frequency, over a predetermined start-up duration. For example, the start-up frequency is higher than the first frequency.

For example, the start-up frequency is higher than 18 Hz. For example, the start-up frequency is comprised between 18 Hz and 20 Hz. For example, the start-up frequency is substantially equal to 19 Hz.

For example, the predetermined start-up duration is comprised between 150 ms and 250 ms. For example, the predetermined start-up duration is comprised between 170 ms and 210 ms. For example, the predetermined start-up duration is substantially equal to 190 ms.

According to a variant of the invention, he phase change in the vibration setting of the powder conveyor device is carried out by directly toggling from the start-up frequency into the first frequency and/or from the first frequency into the second frequency and/or from the second frequency into the second similar frequency and/or from the second similar frequency into a zero frequency and/or from a zero frequency into the third frequency, and/or from the third frequency into a zero frequency.

In other words, a curve of the frequency as a function of the filling ratio or of time, representing the changes in the vibration frequency control sequence could be stairstep-like shaped.

In other words, upon a phase change, the frequency switches from one value into another value without passing through intermediate frequency values.

For example, upon a switch from the first phase into the second phase, the vibration frequency of the conveyor device switches from the first frequency into the second frequency, without passing through intermediate frequency values.

Advantageously, this allows reaching the desired amount of powder more rapidly.

According to a variant of the invention, the phase change in the vibration setting of the powder conveyor device is carried out by linearly toggling from the start-up frequency into the first frequency and/or from the first frequency into the second frequency and/or from the second frequency into the second similar frequency and/or from the second similar frequency into a zero frequency and/or from a zero frequency into the third frequency, and/or from the third frequency into a zero frequency.

In other words, a curve of the frequency as a function of the filling ratio or of time, representing the changes in the vibration frequency control sequence could comprise inclined curve portions between the plateaus.

In other words, during a phase change, the frequency switches from one value to another progressively, that is to say by passing through intermediate values.

For example, upon switching from the first phase into the second phase, the vibration frequency of the conveyor device switches from the first frequency into the second frequency, through intermediate frequency values.

Advantageously, this allows reaching the desired amount of powder in a more accurate manner.

The control sequence according to any of the variants hereinabove, as well as the first, second, third frequencies and/or the start-up frequency and/or second similar frequency are advantageously selected prior to bringing the conveyor device to vibrate, that is to say off production.

The vibration frequency control sequence allows ensuring a filling of the container with the pyrotechnic charge that is initially rapid, and then progressively reduced until reaching the desired amount of powder. The production rate of a production line implementing a vibration frequency control sequence as described hereinabove is increased.

According to one aspect, the filling system further comprises a selection device, the selection device including a collector vat and a lower funnel.

According to one aspect, the collector vat is configured to collect the powder of the basin when the latter is wrongly dosed. For example, the collector vat is configured to collect the powder disposed in the basin when the measured amount of powder exceeds the desired amount of powder.

For example, the collector vat is configured to collect the powder disposed in the basin when the measured amount of powder exceeds the predetermined setpoint value plus the predetermined tolerance.

According to one aspect, the lower funnel is configured to enable the introduction of the powder disposed in the basin into the container, when the measured amount of powder contained in the basin corresponds to the desired amount of powder.

For example, the basin is configured to perform a rotation by about 180° to pour the powder into the collector vat or into the lower funnel.

According to one aspect, the method comprises:
a step of measuring the amount of powder contained in the basin,
when the amount of powder contained in the basin is equal to a predetermined value corresponding to the desired amount of powder, a step of checking up the position of the selection device in which it is checked that the basin is disposed opposite the lower funnel.

Thanks to these steps of the method, the lower funnel collects the powder in order to introduce it into the container only when the amount of powder contained in the basin corresponds to the desired amount of powder. Thus, the number of pyrotechnic charges considered to be non-compliant at the outlet of the production chain is reduced.

According to one aspect, if the basin is not positioned opposite the lower funnel, the method comprises a step of conveying the lower funnel opposite the basin.

According to another variant of the method, the method comprises:
when the amount of powder contained in the basin is not equal to the predetermined value corresponding to the desired amount of powder, a step of checking up that the position of the selection device in which it is checked that the basin is disposed opposite the collector vat.

Thanks to this step of the method, it is possible to collect the wrongly dosed content of the basin, which allows using this powder again.

According to one aspect, if the basin is not positioned opposite the collector vat, the method comprises a step of conveying the collector vat opposite the basin.

According to another variant of the method, the filling system comprises said lower funnel, called first lower funnel, and a second lower funnel for collecting the powder poured into the first funnel.

The second lower funnel is configured to be coupled to the container so as to be able to introduce the powder into the container while limiting losses.

According to one aspect, the method comprising:
a step of conveying the container of the pyrotechnic charge opposite the second lower funnel,
a step of coupling the second lower funnel with the container of the pyrotechnic charge.

It should be understood that coupling of the second lower funnel with the container is carried out when it has been determined that the basin contained an amount of powder corresponding to the desired amount of powder.

It should be understood that the first lower funnel is disposed opposite the second lower funnel when it has been determined that the basin contained an amount of powder corresponding to the desired amount of powder.

Thanks to these steps of the method, it is possible to carry out coupling of the container with the second lower funnel only once it has been determined that the vessel contained an amount of powder corresponding to the desired amount of powder.

According to one aspect, the filling system comprises an upper funnel for collecting the powder contained in the basin. The upper funnel is configured to be disposed under the basin.

According to one aspect, when the amount of powder contained in the basin corresponds to the desired amount of powder, the first lower funnel is disposed under the upper funnel.

According to one aspect, when the amount of powder contained in the basin does not correspond to the desired amount of powder, the collector vat is disposed under the upper funnel.

According to another embodiment of the invention, the filling system is made equipotential so as to avoid the electrostatic retention of powder grains.

According to another embodiment of the invention, the method comprises a step of vibration setting in which at least one of the funnels is set in constant vibration.

For example, at least one of the funnels is brought to vibrate using at least one vibrational actuator such as a piezoelectric actuator.

Advantageously, each funnel is brought to vibrate.

According to a variant of the method, the at least one reservoir for dispensing a pyrotechnic charge is associated to two powder measuring devices, each powder measuring device being associated to a device for conveying powder from the reservoir up to a basin of the corresponding measuring device, the step of regulating the powder flow rate being implemented when the powder is conveyed by either one of the conveyor devices.

Thus, the production rate of pyrotechnic charges is increased.

According to one aspect, the filling system comprises for each of the basins, an upper funnel for collecting the powder disposed opposite the corresponding basin.

According to one aspect, said method comprises:
  a step of measuring the amount of powder contained in each basin of the measuring devices,
  when the amount of the powder contained in at least one basin corresponds to the desired amount of powder, a step of checking up the position of the selection device in which it is checked that the basin containing the amount of powder corresponding to the desired amount of powder is disposed opposite the lower funnel.

Thus, in addition to the above-mentioned advantages, the production rate is not affected if the amount of powder contained in one of the basins does not correspond to the desired amount of powder.

It should be understood that when each basin is properly dosed, any one of these basins is retained so as to pour the powder contained therein into the container of the pyrotechnic charge.

According to one aspect, the above-described method is configured to be implemented by a first filling system configured to fill the container with a first powder type, and a second filling system configured to fill the container with a second powder type.

For example, the first powder type is the slow powder and the second powder type is the live powder, or vice versa.

According to one aspect, the container is configured to be conveyed towards the first filling system so as to be filled with the first powder type, then to be conveyed towards the second filling system so as to be filled with the second powder type.

Advantageously, the pyrotechnic charge is provided for a needleless injection device where an active substance thereof contained in a reservoir of the injection device could advantageously be selected from the group comprising the following active substances:
  Methotrexate,
  Adrenaline,
  Sumatriptan,
  Hydrocortisone,
  Naloxone,
  Midazolam,
  Apomorphine,
  Methylnaltrexone bromide,
  Phytomenadione,
  Chlorpromazine hydrochloride,
  Zuclopenthixol acetate,
  Danaparoid sodium,
  Enoxaparin sodium,
  Estradiol cypionate,
  Medroxyprogesterone acetate,
  Medroparine calcium,
  Methylprednisolone acetate,
  Heparin calcium,
  Terbutaline.

Advantageously, the amount of powder is selected so as to allow for a successful injection, the jets at the outlet of an injection nozzle should be delivered according to an injection pressure over a predetermined injection time guaranteeing the injection of the desired amount of active substance.

The present disclosure further concerns a system for filling a container with a pyrotechnic charge, the filling system comprising at least:
  a reservoir for dispensing a pyrotechnic powder,
  a device for measuring this powder, and
  a device for conveying this powder from the reservoir up to a basin of the measuring device.

The filling system comprises at least one vibrational actuator, such as a piezoelectric actuator, coupled to the device for conveying this powder.

Without limitation, the vibrational actuator may be of the electric, mechanical or pneumatic type.

According to one aspect, the filling system is adapted to implement the method as defined hereinabove.

According to one aspect, the filling system further comprises an electronic controller configured to control the vibrational actuator so as to implement a vibration frequency control sequence, the vibration frequency being inversely proportional to the filling ratio of the container of the pyrotechnic charge.

The vibration frequency control sequence is in accordance with any one of the aforementioned features.

Advantageously, the measuring device is mechanically linked directly to a neutral reference frame, such as the ground. Thus, it is possible to ensure that the measurement of the amount of powder contained in the basin is not degraded by mechanical disturbances of the elements constituting the filling system.

It should be understood that the filling system comprises a main frame, this main frame being linked to the reference frame separately from a frame of the measuring device so that the measuring device is mechanically isolated from the other constituent elements of the filling system.

Even more advantageously, the measuring device is linked to the neutral reference frame by an anti-vibration neutral connection. Such a flexible connection may be achieved by one or several vibration dampers.

Such a configuration of the filling system allows improving the accuracy of the measuring device whose mechanical disturbances of the elements constituting the filling system do not affect the measuring device.

Advantageously, the at least one vibrational actuator is mechanically linked directly to a neutral reference frame, such as the ground. It is then possible to limit the propagation of these vibrations to other elements constituting the filling system which might distort the measurement of the measured amount of powder.

According to an embodiment of the filling system, the at least one reservoir for dispensing a pyrotechnic powder is associated to two powder measuring devices, each powder measuring device being associated to a device for conveying powder from the reservoir up to a basin of the corresponding measuring device.

Advantageously, each measuring device of the filling system may comprise the previous features.

According to one aspect, the filling system comprises for each basin of the measuring devices an upper funnel for collecting the powder contained in the corresponding basin.

According to one aspect, the filling system further comprising a selection device, the selection device including a collector vat and a lower funnel, the selection device is configured for setting the collector vat or the lower funnel in position opposite the basin.

According to one aspect, the electronic controlled is configured to compare the measurement of the amount of powder contained in the basin with a desired amount of powder.

According to one aspect, when the measured amount of powder in the basin corresponds to the desired amount of powder, the electronic controller is configured to control the selection device so as to check that the lower funnel is disposed opposite the basin.

According to one aspect, in this case, if the lower funnel is not placed opposite the basin, the electronic controller is configured to control the selection device so as to place the lower funnel opposite the basin.

According to one aspect, when the measured amount of powder in the basin does not correspond to the desired amount of powder, the electronic controller is configured to control the selection device so as to check that the collector vat is placed opposite the basin.

According to one aspect, in this case, if the collector vat is not placed opposite the basin, the electronic controller is configured to control the selection device so as to place the collector vat opposite the basin.

According to an embodiment of the filling system, the filling system comprises said lower funnel, called first lower funnel, and a second lower funnel for collecting the powder poured into the first lower funnel, in that the second lower funnel being intended to be coupled with the container of the pyrotechnic charge conveyed beforehand.

According to an embodiment of the filling system, an outlet opening of the second lower funnel is beveled so as to facilitate coupling thereof with an inlet opening of the container of the pyrotechnic charge.

According to one aspect, when the measured amount of powder in the basin corresponds to the desired amount of powder, the electronic controller is configured to control a line for conveying the container so as to place the container opposite the first lower funnel.

According to one aspect, when the measured amount of powder in the basin corresponds to the desired amount of powder, the electronic controller is configured to control a line for conveying the container so as to place the container opposite the second lower funnel.

According to one aspect, when the measured amount of powder in the basin corresponds to the desired amount of powder, the electronic controller is configured to control the second lower funnel so that it is coupled with the container conveyed before The present disclosure further concerns a filling set comprising:
- a first filling system in accordance with any one of the aforementioned features;
- a second filling system in accordance with any one of the aforementioned features;
- the first filling system being configured to fill a container with a pyrotechnic charge with a first type of pyrotechnic powder and the second filling system being configured to fill the container with the pyrotechnic charge with a second type of pyrotechnic powder.

Figure 2:
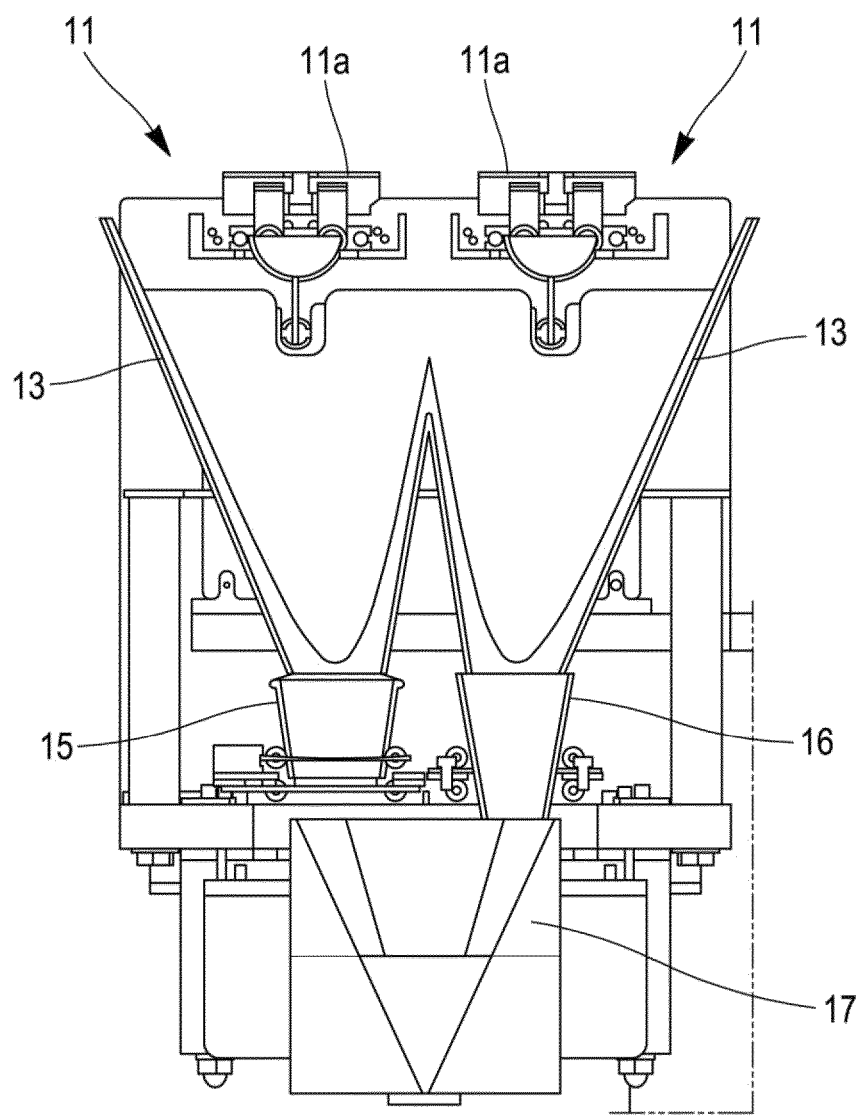
Figure 3:
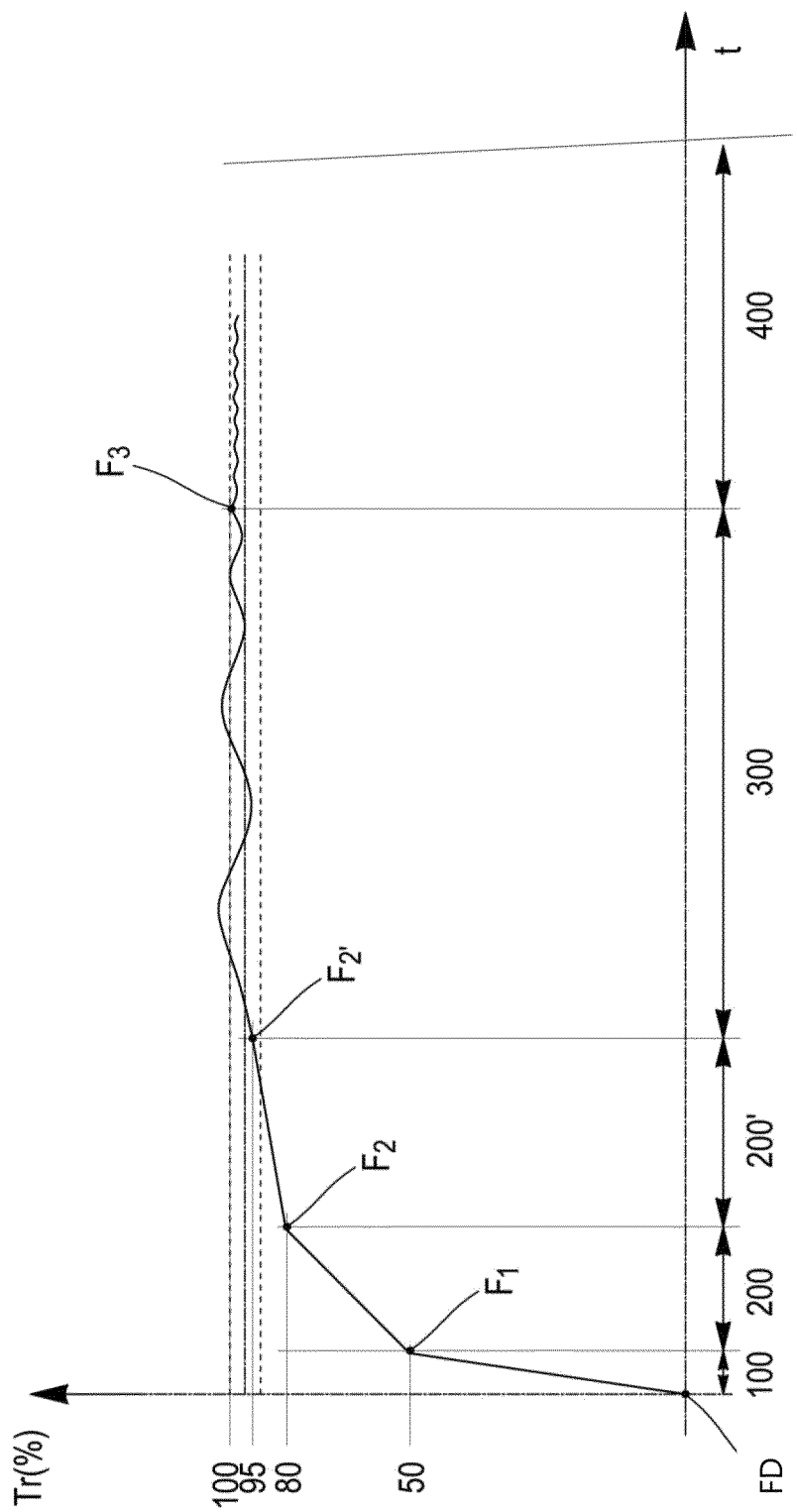

Other aspects, objects and advantages of the invention will appear upon reading the following detailed description of preferred embodiment thereof provided as non-limiting examples, made with reference to the following appended drawings:

FIG. 1 schematically represents a filling system,
FIG. 2 schematically represents a side view of the filling system, FIG. 3 illustrates a vibration frequency control sequence of the dispenser system.

In FIGS. 1 and 2, the system 1 for filling a container 2 with a pyrotechnic charge adapted to implement the method as defined in the present document is represented.

The filling system 1 is controlled using an electronic controller configured to carry out the steps of the method described in the present document.

The filling system 1 is represented mounted on a production line for mass filling of containers 2 with pyrotechnic charges.

In FIG. 1, the progress direction of such a production line is represented by a longitudinal direction L.

In FIG. 2, the progress direction is represented by a direction T orthogonal to the longitudinal direction L.

A vertical direction V orthogonal to each of the longitudinal L and orthogonal T directions is also represented.

As represented, the filling system 1 comprising at least one reservoir 10 for dispensing a pyrotechnic powder, a device 11 for measuring this powder, and a device 12 for conveying this powder from the reservoir 10 up to a basin 11a of the measuring device 11.

A vibrational actuator 12a, such as a piezoelectric actuator, is coupled to the device for conveying this powder.

The vibrational actuator 12a then generates vibrations according to a vibration frequency that could be variable.

Advantageously, the measuring device 11 is mechanically linked directly to a neutral reference frame R0, such as the ground. The mechanical dependence to such a reference frame allows ensuring that the measurement of the amount of powder contained in the basin 11a is not altered by mechanical disturbances from the elements constituting the filling system 1.

Similarly, the at least one vibrational actuator 12a is mechanically linked directly to a neutral reference frame R0, such as the ground. It is then possible to limit the propagation of these vibrations to other elements constituting the filling system 1 which could distort the measurement of the amount of powder contained in the basin.

Advantageously, the conveyor device 12 may comprise a hopper.

The measuring device 11 may be formed by a scale to which the basin 11a is fastened forming a doser, herein represented in the form of a spoon.

As represented in FIG. 2, the filling system 1 comprises two powder measuring devices 11, each powder measuring device 11 being associated to a device 12 for conveying powder from the reservoir 10 up to a basin 11a of the corresponding measuring device 11.

Advantageously, a reservoir 10 may be provided for each measuring device 11 and conveyor device 12.

Each basin 11a of the measuring devices 11 is associated to an upper funnel 13 for collecting the powder contained in the corresponding basin 11a.

A device for selecting basins 11a includes a collector vat 15 and a lower funnel 16. Advantageously, the selection device is intended to position the collector vat 15 and/or the lower funnel 16 opposite the upper funnel(s) 13.

For this purpose, the collector vat 15 and/or the lower funnel 16 of the selection device are guided in translation according to the progress direction of the production line.

The filling system comprises said lower funnel, called first lower funnel 16, and a second lower funnel 17 for collecting the powder poured into the first lower funnel 16, the second lower funnel 17 is intended to be coupled with the container 2 of the pyrotechnic charge conveyed beforehand.

An outlet opening 17*a* of the second lower funnel 17 is beveled to facilitate coupling thereof with an inlet opening 2*a* of the container 2 of the pyrotechnic charge.

The steps of the method allowing filling the container with the pyrotechnic charge described in the present document will now be described.

When the powder is conveyed, a step of regulating the powder flow rate is carried out in which each conveyor device 12 is brought to vibrate according to a vibration frequency control sequence, the vibration frequency being inversely proportional to the filling ratio of the container 2 of the pyrotechnic charge.

FIG. 3 illustrates such a vibration frequency control sequence represented by the filling ratio Tr in percentage proportional to the filling time.

The vibration frequency control sequence comprises a first phase 100 in which the conveyor device 12 is brought to vibrate according to a first frequency F1 comprised between 16 Hz and 18 Hz, preferably 17 Hz, until reaching a first content ratio of the container comprised between 50% and 80%, preferably at least equal to 75%, of the desired filling ratio of the container, then a second phase 200 in which the conveyor device 12 is brought to vibrate according to a second frequency F2 comprised between 13 Hz and 16 Hz, preferably 15 Hz, until reaching a second filling ratio of the container comprised between 80% and 95%, preferably at least equal to 90%, of the desired filling ratio of the container.

In this example, the vibration frequency control sequence comprises a second similar phase 200' in which the conveyor device is brought to vibrate according to a second similar frequency F2' preferably comprised between 8 Hz and 13 Hz, preferably 10 Hz, said second similar frequency F2' being lower than said second frequency F2.

The vibration frequency control sequence then comprises a third phase 300 in which the vibration of the conveyor device 12 is stopped until stabilisation of the measured amount of powder, for example over a time period substantially equal to 2000 ms.

Following this third phase, if the measured amount of powder corresponds to the desired amount of powder, the vibration frequency control sequence is terminated and the basin is considered to be properly dosed and the method could be carried on until filling of the container with this powder dose.

If the measured amount of powder is larger than the desired amount of powder, the vibration frequency control sequence is terminated, the basin is considered to be wrongly dosed and the method could be carried on until discarding or recovering this powder dose.

Following the third phase 300, if the measured amount of powder is smaller than the desired amount of powder, for example when the filling ratio is comprised between 95 and 98%, a fourth phase 40 could be carried out, in which the conveyor device 12 could advantageously be brought to vibrate according to a third frequency F3 comprised between 10 Hz and 20 Hz, and more preferably equal to 14 Hz, over a predetermined time period, for example equal to 1000 ms, then a new stabilisation phase, herein a fifth phase, similar to the third phase.

Following this fifth phase, if the measured amount of powder corresponds to the desired amount of powder, the vibration frequency control sequence is terminated and the basin is considered to be properly dosed and the method could be carried on until filling the container with this powder dose.

Of the measured amount of powder is smaller than the desired amount of powder, for example when the filling ratio is comprised between 95 and 98%, the fourth and fifth phases could be repeated until reaching the desired amount of powder.

If the measured amount of powder is larger than the desired amount of powder, the vibration frequency control sequence is terminated, the basin is considered to be properly dosed and the method could be carried on until discarding or recovering this powder dose.

Moreover, it is possible to carry out an initial phase where the conveyor device 12 is brought to vibrate according to a start-up frequency FD over a predetermined start-up time period, for example equal to 190 ms, prior to the first phase 100, that being so to allow reaching the desired filling ratio more rapidly.

For example, the start-up frequency FD is higher than 18 Hz. For example, the start-up frequency FD is comprised between 18 Hz and 20 Hz. For example, the start-up frequency FD is substantially equal to 19 Hz.

The first frequency is called «very high speed frequency», the second frequency is called «high speed frequency», the second similar frequency is called «low speed frequency» and the third frequency and the start-up frequency are called «boost frequencies».

Starting from the third phase 300, the powder grains are conveyed into the continuous basin by pouring following the last vibration phase. In this third phase 300, the measurement of the amount of powder contained in the basin settles down over time.

Concurrently with the step of regulating the powder flow rate, a step of measuring the powder contained in each basin 11*a* of the measuring devices 11 is carried out.

When the measurement of the contained powder in at least one basin 11*a* is equal to a predetermined value corresponding to the desired amount of powder to fill the container 2 with the pyrotechnic charge, a step of checking up the position of the selection device is carried out in which it is checked that the upper funnel 13 associated to said basin 11*a* containing said predetermined value is disposed opposite the lower funnel 17.

When at least one basin 11*a* or each basin 11*a* is properly dosed, any one of these basins 11*a* is retained to pour the powder contained therein into the container 2 of the pyrotechnic charge.

When the measurement of the powder contained in at least one basin 11*a* is not equal to the predetermined value, a step of checking up the position of the selection device is carried out in which it is checked that the upper funnel 13 associated to said basin 11*a* that does not contain said predetermined value is disposed opposite the collector vat 15.

When the collector vat 15 is not opposite the upper funnel 13, the selection device is displaced to achieve this position setting.

The wrongly dosed content of the basin 11*a* is then received without interrupting the production line.

When the content of the basin 11*a* is properly dosed, a step of checking up the position of the selection device is carried out in which it is checked that the upper funnel 13 associated to said properly dosed basin 11*a* is disposed opposite the first lower funnel 16.

When the first lower funnel 16 is not opposite the upper funnel 13, the selection device is displaced to achieve this position setting.

Then, a step of conveying the container 2 of the pyrotechnic charge opposite the second lower funnel 17 is carried out, then a step of coupling the second lower funnel 17 with the container 2 of the pyrotechnic charge.

It should be understood that a properly dosed basin 11a corresponds to the basin 11a where the measurement of the powder contained therein is equal to a predetermined value corresponding to the desired amount of powder.

In the coupling step, the second lower funnel 17 is displaced vertically to achieve this coupling.

Then, the powder content of the basin is poured into the corresponding upper funnel 13 and it is conveyed by gravity up to the container of the pyrotechnic charge conveyed beforehand. Herein, the basin is formed by a spoon whose stem is configured to be rotated to pour its content. To this end, the measuring device may comprise a motor provided to this end.

Of course, the funnels by which the powder is conveyed are disposed successively next to one another to enable this transfer.

The funnels may be brought to vibrate to facilitate this transfer and avoid any powder accumulation phenomena during this transfer.

It is also possible to provide for making the funnels equipotential to avoid all electrostatic phenomena.

Of course, the invention is not limited to the examples that have just been described and many arrangements could be brought to these examples yet without departing from the scope of the invention. In particular, the different features, shapes, variants and embodiments of the invention could be associated with one another according to various combinations to the extent that these are not incompatible or do not exclude each other. In particular, all of the previously described variants and embodiments could be combined together.

The invention claimed is:

1. A filling method for filling a container of a pyrotechnic charge using a filling system, the filling system comprising at least:
    a reservoir for dispensing a pyrotechnic powder,
    a measuring device for measuring the pyrotechnic powder, and
    a powder conveyor device for conveying the pyrotechnic powder from the reservoir to a basin of the measuring device,
    wherein said filling method comprises:
    when the pyrotechnic powder is conveyed, a step of regulating the powder flow rate wherein the powder conveyor device is set in vibration according to a vibration frequency control sequence, the vibration frequency being inversely proportional to the filling ratio of the container of the pyrotechnic charge.

2. The filling method according to claim 1, wherein the vibration frequency control sequence comprises at least:
    a first phase wherein the powder conveyor device is set in vibration according to a first frequency until reaching a first filling ratio of the container, then
    a second phase wherein the powder conveyor device is set in vibration according to a second frequency until reaching a second filling ratio of the container,
    the first frequency being higher than the second frequency.

3. The filling method according to claim 1, wherein the filling system comprises a selection device, the selection device including a collector vat and a lower funnel configured to enable filling of the container,
    said method comprising:
    a step of measuring an amount of pyrotechnic powder contained in the basin of the measuring device,
    when the amount of the pyrotechnic powder contained in the basin corresponding to a desired amount of the pyrotechnic powder to be introduced into the container of the the pyrotechnic charge, a step of checking up a position of the selection device to conform that the basin is facing the lower funnel.

4. The filling method according to claim 3, comprising:
    when the amount of the pyrotechnic powder contained in the basin does not correspond to the desired amount of the pyrotechnic powder, a step of checking up the position of the selection device to conform that the basin is facing the collector vat.

5. The filling method according to claim 3, wherein:
    the filling system comprises a second lower funnel for collecting the pyrotechnic powder poured into the lower funnel hereinafter called «first lower funnel»,
    the filling method comprising:
    a step of conveying the container of the pyrotechnic charge in front of the second lower funnel,
    a step of coupling the second lower funnel with the container of the pyrotechnic charge.

6. The filling method according to claim 3, comprising a step of vibration setting wherein at least the first lower funnel is set in constant vibration.

7. The filling method according to claim 1, wherein the filling system is equipotential such that an electrostatic retention of grains of the pyrotechnic powder is avoided.

8. The filling method according to claim 1, wherein the reservoir for dispensing the pyrotechnic powder is associated with two measuring devices, each measuring device being associated with a powder conveyor device for conveying the pyrotechnic powder from the reservoir to a basin of the corresponding measuring device, the step of regulating the pyrotechnic powder flow rate being implemented when the pyrotechnic powder is conveyed by one of the conveyor devices and/or both the conveyor devices.

9. The filling method according to claim 8, comprising:
    a step of measuring an amount of the pyrotechnic powder contained in each basin of the measuring devices,
    when the amount of the pyrotechnic powder contained in at least one basin corresponds to a desired amount of the pyrotechnic powder, a step of checking up a position of the selection device to conform that the basin containing the amount of the pyrotechnic powder corresponding to the desired amount of the pyrotechnic powder is facing a first lower funnel.

10. A filling system for filling a container of a pyrotechnic charge, comprising at least:
    a reservoir for dispensing a pyrotechnic powder,
    a measuring device for measuring the pyrotechnic powder, and
    a powder conveyor device for conveying the pyrotechnic powder from the reservoir to a basin of the measuring device,
    wherein the filling system comprises a vibrational actuator, coupled to the powder conveyor device for conveying the pyrotechnic powder,
    wherein the filling system further comprises a controller configured to implement a vibration frequency control sequence, the vibration frequency being inversely proportional to the filling ratio of the container of the pyrotechnic charge.

11. The filling system according to claim 10, comprising a selection device including a collector vat and a lower funnel,
    the selection device is configured to set the collector vat or the lower funnel in a position facing the basin.

12. The filling system according to claim 11, comprising said lower funnel, hereinafter called "first lower funnel", and a second lower funnel for collecting the pyrotechnic powder poured into the first lower funnel, wherein the second lower funnel is configured to be coupled with the container of the pyrotechnic charge conveyed beforehand.

13. The filling system according to claim 10, wherein the reservoir for dispensing the pyrotechnic powder is associated with two powder measuring devices, each of the powder measuring devices being associated with a powder conveyor device for conveying the pyrotechnic powder from the reservoir to a basin of the corresponding measuring device.

14. A filling set comprising:
a first filling system according to claim 10;
a second filling system according to claim 10;
the first filling system being configured to fill the container of the pyrotechnic charge with a first type of pyrotechnic powder and the second filling system being configured to fill the container of the pyrotechnic charge with a second type of pyrotechnic powder.

\* \* \* \* \*